(12) United States Patent
Cacciaglia et al.

(10) Patent No.: US 8,742,172 B2
(45) Date of Patent: Jun. 3, 2014

(54) POLYMORPHIC FORMS OF N-[4-(TRIFLUOROMETHYL)BENZYL]-4-METHOXYBUTYRAMIDE

(75) Inventors: Roberto Cacciaglia, Ospedaletti (IT); Massimo Ferrari, Cenate Sotto (IT)

(73) Assignee: Laboratorio Farmaceutico C.T. S.R.L., Sanremo (IT)

( * ) Notice: Subject to any disclaimer, the term of this patent is extended or adjusted under 35 U.S.C. 154(b) by 0 days.

(21) Appl. No.: 12/742,304

(22) PCT Filed: Nov. 12, 2008

(86) PCT No.: PCT/EP2008/065367
§ 371 (c)(1),
(2), (4) Date: May 11, 2010

(87) PCT Pub. No.: WO2009/062949
PCT Pub. Date: May 22, 2009

(65) Prior Publication Data
US 2010/0261797 A1 Oct. 14, 2010

(30) Foreign Application Priority Data

Nov. 13, 2007 (EP) .................................. 07120551

(51) Int. Cl.
*C07C 233/00* (2006.01)
*A01N 37/18* (2006.01)

(52) U.S. Cl.
USPC .......................................... 564/202; 514/625

(58) Field of Classification Search
None
See application file for complete search history.

(56) References Cited

U.S. PATENT DOCUMENTS

| | | | |
|---|---|---|---|
| 6,331,649 B1 | 12/2001 | Narizuka et al. | |
| 2002/0013500 A1 | 1/2002 | Narizuka et al. | |

FOREIGN PATENT DOCUMENTS

| | | |
|---|---|---|
| EP | 0 932 597 | 8/1999 |
| JP | 2000-273069 A | 10/2000 |
| JP | 2001-294559 A | 10/2001 |

OTHER PUBLICATIONS

Ottani et al., "Preference for Palatable Food is Reduced by the Gamma-Hydroxybutyrate Analague GET73, in rats" Pharmacological Research, Academic Press, London, GB, vol. 55, No. 4, Apr. 4, 2007, pp. 271-279, XP022014497, ISSN: 1043-6618 Abstract.
Caira M R: "Crystalline Polymorphism of Organic Compounds" Topics in Current Chemistry, Springer, Berlin, DE, vol. 198, 1998, pp. 163-208, XP001156954 ISSN: 0340-1022.

*Primary Examiner* — Paul A Zucker
*Assistant Examiner* — Jennifer C Sawyer
(74) *Attorney, Agent, or Firm* — DLA Piper LLP (US); Stephanie X. Wang

(57) ABSTRACT

Crystalline polymorphic forms of a compound of formula N-[4-(trifluoromethyl)benzyl]-4-methoxybutyramide are described. The two polymorphic forms, named polymorphic Form A and polymorphic Form B, can be used in the treatment of drug addiction and alcoholism and have very good stability. Methods for preparing the polymorphic forms are also described.

16 Claims, 8 Drawing Sheets

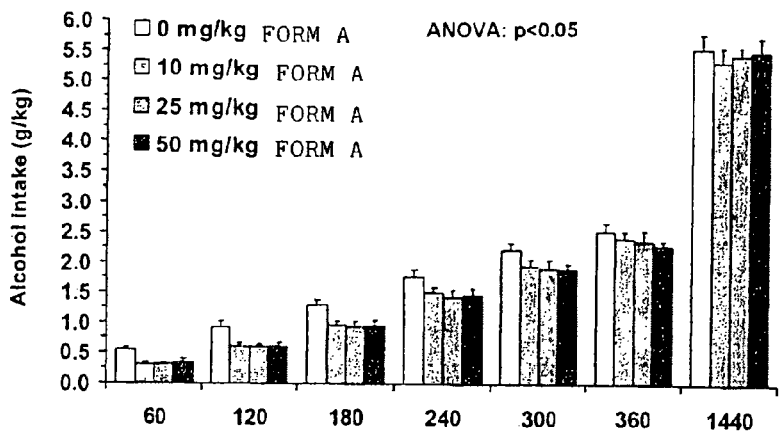

Figure 8A

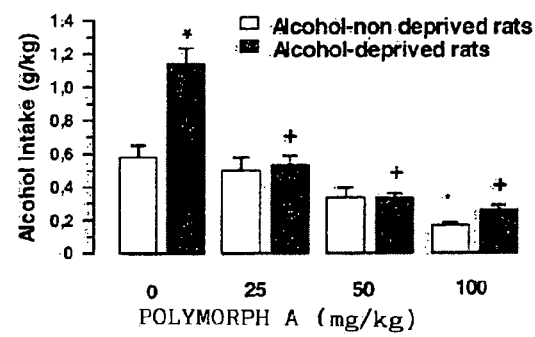

Figure 8B

*: with respect to 0 mg/kg FORM A-treated alcohol-nondeprived rats
+: with respect to 0 mg/kg FORM A-treated alcohol-deprived rats Data are referred to first hour or re-access to alcohol (when ADE in sP rats is maximally pronounced)

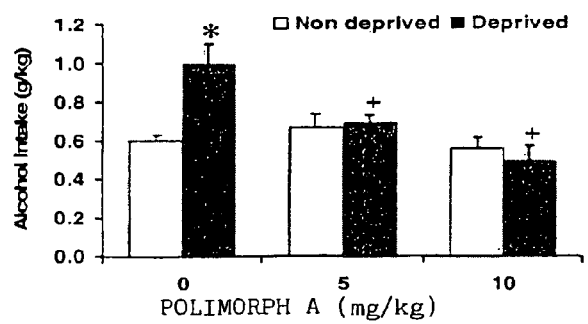

Figure 8C

*: with respect to 0 mg/kg FORM A-treated alcohol-nondeprived rats
+: with respect to 0 mg/kg FORM A-treated alcohol-deprived rats Data are referred to first hour or re-access to alcohol (when ADE in sP rats is maximally pronounced)

POLYMORPHIC FORMS OF N-[4-(TRIFLUOROMETHYL)BENZYL]-4-METHOXYBUTYRAMIDE

FIELD OF THE INVENTION

The present invention concerns two new polymorphic forms of a compound of Formula (I)

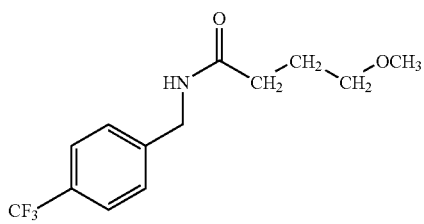

(I)

namely N-[4-(trifluoromethyl)benzyl]-4-methoxybutyramide, and their use in the treatment of drug addiction and, particularly, in the treatment of alcoholism.

STATE OF THE ART

N-[4-(trifluoromethyl)benzyl]-4-methoxybutyramide has been disclosed for the first time in European patent EP 0 932 597 B1 as being part of a group of amides useful in the treatment of drug addiction and in the alcoholism.

According to such a patent, N-[4-(trifluoromethyl)benzyl]-4-methoxybutyramide, having 4-trifluoromethylbenzyl residue exhibited optimal properties in terms of neuropharmacological activity, when compared with salts of γ-hydroxybutyric acid (GHB), well known in the treatment of alcoholism. In particular, in the evaluation of effects on the motor activity of the rat, it had showed properties of potency and duration of action, which were better than GHB and still better than other amides having different residues in the structure.

In view to its optimal neuropharmacological activity, therefore, N-[4-(trifluoromethyl)benzyl]-4-methoxybutyramide was requested in high purity and high yields in order to be used in pharmacology.

Firstly, the inventors of the present invention have tried to obtain N-[4-(trifluoromethyl)benzyl]-4-methoxybutyramide by following the preparation described in the patent.

Specifically, according to EP 0 932 597 B1, the compound was prepared by following the general method of synthesis described on page 8 of the patent, which provided for the following steps: A) reacting 4-alkoxybutyric acid ester with a suitable amine in the presence of NH$_4$Cl at temperature of 160-170° C., thus obtaining the crude product, B) cromatographing the crude on silica gel eluting with cycloexane/ethylacetate and finally C) crystallizing from CH$_2$Cl$_2$/Et$_2$O. Following this procedure, however, the present inventors found out that, even if they obtained the wished compound, it had each time different physical-chemical characteristics. The general method of synthesis indicated in EP 0 932 597 B1 therefore revealed itself to be of scarce reproducibility and due to the purification step B) also very expensive and therefore not suitable for the preparation of N-[4-(trifluoromethyl)benzyl]-4-methoxybutyramide on an industrial scale.

SUMMARY

By trying to solve the problem of the reproducibility of the process of preparation of N-[4-(trifluoromethyl)benzyl]-4-methoxybutyramide, the present inventors have surprisingly found out that the compound can be in different polymorphic forms. Specifically, in developing the preparation and distillation and analyzing each time the obtained product, they found out two novel two polymorphic forms of N-[4-(trifluoromethyl)benzyl]-4-methoxybutyramide, Form A e Form B, having different crystal packing.

Therefore, the present invention provides in one aspect a polymorphic Form A of N-[4-(trifluoromethyl)benzyl]-4-methoxybutyramide of formula:

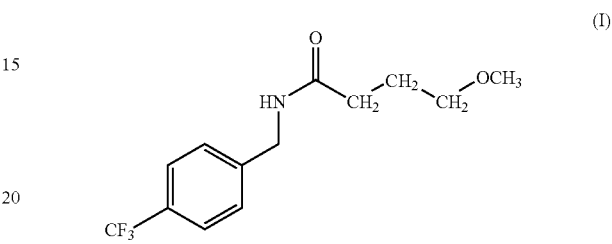

(I)

having the following peaks at the diffraction degrees (2-theta) in the X-ray powder diffraction pattern ±0.2:
9.7; 12.0; 18.0; 24.1; 25.9.

In a further aspect the present invention provides for a polymorphic Form B of the compound of formula (I), having the following peaks at the diffraction degrees in the X-ray powder diffraction pattern ±0.2:
11.7; 19.8; 22.3; 23.6.

Furthermore, the inventors also found out a process capable to produce the two novel polymorphic Forms A and B in an always reproducible and stable way and in high purity without the need of a chromatographic purification step.

In a still further aspect, therefore the present invention concerns a process for preparing the polymorphic form A of N-[4-(trifluoromethyl)benzyl]-4-methoxybutyramide comprising the following steps:

i) reacting 4-trifluoromethylbenzylamine with methyl 4-methoxybutyrate in the presence of a catalyst thus obtaining crude N-[4-(trifluoromethyl)benzyl]-4-methoxybutyramide; and ii) obtaining crystalline polymorphic Form A from a solution of crude N-[4-(trifluoromethyl)benzyl]-4-methoxybutyramide in an organic solvent, being said solution seeded with the polymorphic Form A of N-[4-(trifluoromethyl)benzyl]-4-methoxybutyramide.

In a still further aspect the present invention concerns a process for preparing the polymorphic Form B of N-[4-(trifluoromethyl)benzyl]-4-methoxybutyramide comprising the following steps:

(i) reacting 4-trifluoromethylbenzylamine with methyl 4-methoxybutyrate in the presence of a catalyst thus obtaining crude N-[4-(trifluoromethyl)benzyl]-4-methoxybutyramide; and (ii) obtaining crystalline polymorphic Form B from a solution of crude N-[4-(trifluoromethyl)benzyl]-4-methoxybutyramide in an organic solvent, being said solution seeded with the polymorphic Form B of N-[4-(trifluoromethyl)benzyl]-4-methoxybutyramide.

Polymorphic Forms A and B of N-[4-(trifluoromethyl)benzyl]-4-methoxybutyramide are useful in the treatment of drug addiction and in the treatment of alcoholism. More particularly, they are useful in reducing the voluntary consumption of ethyl alcohol and in the treatment of the abstinences syndrome. Furthermore, the aforesaid polymorphic Form A and polymorphic Form B are also useful in the treatment of the crises of abstinence from habit-forming drugs, such as heroin, cocaine, morphine and psychoactive drugs. Therefore, the present invention concerns also a polymorphic Form A of N-[4-(trifluoromethyl)benzyl]-4-methoxybutyramide for use as a medicament and also a polymorphic Form B of N-[4-(trifluoromethyl)benzyl]-4-methoxybutyramide for use as a medicament.

In another aspect, the present invention also relates to a pharmaceutical composition comprising as active agent an effective amount of a polymorphic Form A of N-[4-(trifluoromethyl)benzyl]-4-methoxybutyramide and a pharmaceutically acceptable carrier and also a pharmaceutical composition comprising as active agent an effective amount of a polymorphic Form B of N-[4-(trifluoromethyl)benzyl]-4-methoxybutyramide and a pharmaceutically acceptable is carrier.

DESCRIPTION OF THE FIGURE

FIG. 8A shows the results of the model of spontaneous alcohol intake in non deprivated sP rats after administration of the polymorphic Form A;

FIG. 8B shows the results of a model of alcohol deprivation effect in non deprivated sP rats after administration of high doses of polymorphic Form A; and FIG. 8C shows the results of a model of alcohol deprivation effect in non deprivated sP rats after administration of low doses of the polymorphic Form A.

DETAILED DESCRIPTION OF THE INVENTION

The invention concerns a new polymorphic form A and a new polymorphic form B of N-[4-(trifluoromethyl)benzyl]-4-methoxybutyramide, having different relevant peaks at the diffraction degrees (2-theta in angular degrees ±0.2°) in the X-ray powder diffraction pattern, specifically 9.7, 12.0, 18.0, 24.1, 25.9 for polymorphic Form A and 11.7, 19.8, 22.3, 23.6 for polymorphic Form B.

Figure 1:
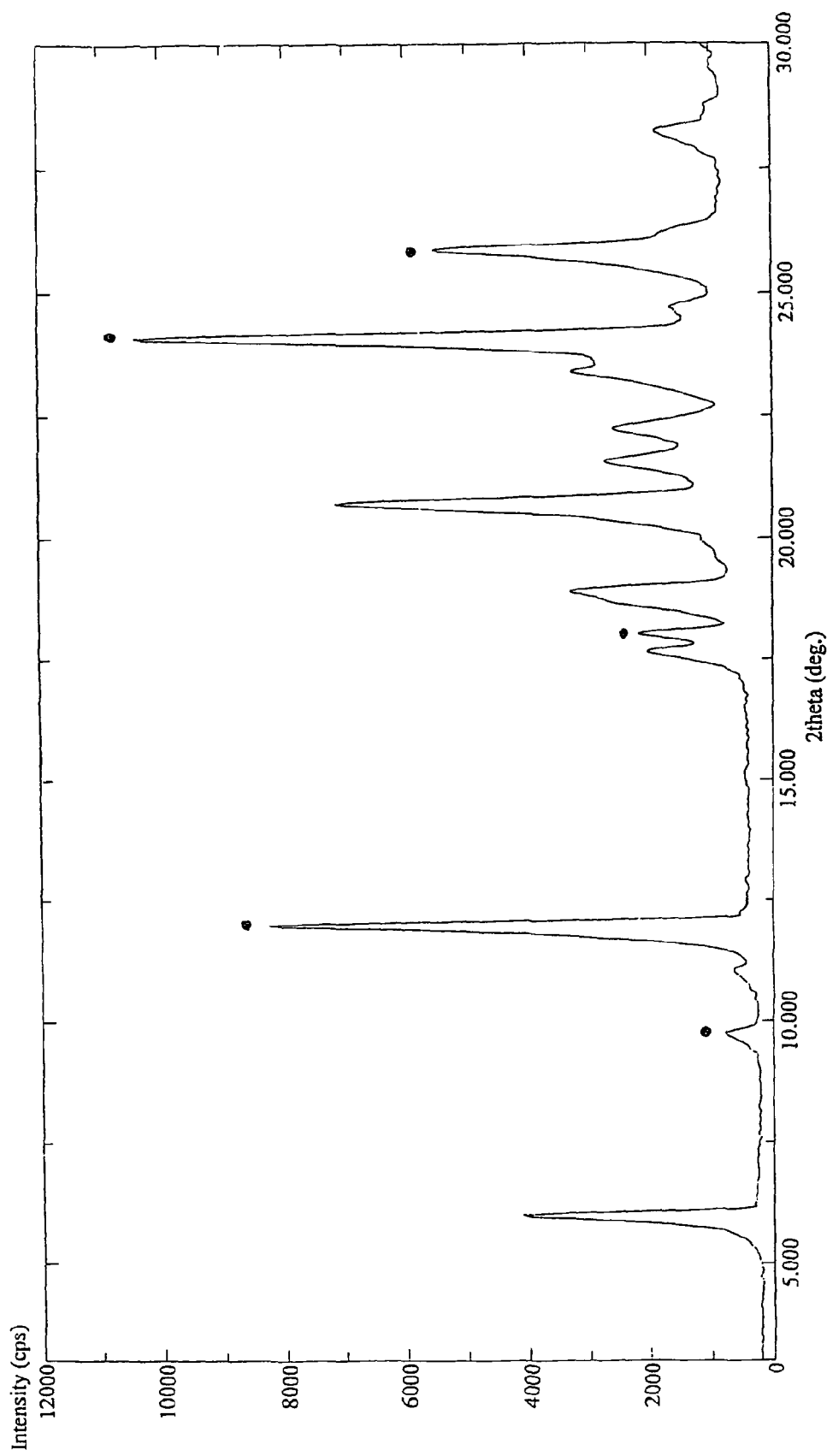
FIG. 1 shows the X-ray powder diffraction pattern of N-[4-(trifluoromethyl)benzyl]-4-methoxybutyramide in the crystalline polymorphic Form A.

More specifically, polymorphic Form A exhibits 18 peaks at the diffraction degrees with the intensity shown below in the Table 1 in the X-ray powder diffraction pattern as depicted in FIG. 1.

TABLE 1

| Peaks of polymorphic Form A (2-theta in angular degrees ±0.2°) | | | |
|---|---|---|---|
| Peak | 2-theta | Intensity (cps) | $I/I_0$ |
| 1 | 6.0 | 4082 | 40 |
| 2 | 9.7 | 797 | 8 |
| 3 | 11.0 | 640 | 7 |
| 4 | 12.0 | 8297 | 80 |
| 5 | 17.6 | 2032 | 20 |
| 6 | 18.0 | 2173 | 21 |
| 7 | 18.7 | 2658 | 26 |
| 8 | 18.9 | 3293 | 32 |
| 9 | 19.6 | 919 | 9 |
| 10 | 20.7 | 7158 | 69 |
| 11 | 21.6 | 2730 | 27 |
| 12 | 22.2 | 2601 | 26 |
| 13 | 23.4 | 3261 | 32 |
| 14 | 24.1 | 10380 | 100 |
| 15 | 24.7 | 1663 | 17 |
| 16 | 25.9 | 5534 | 54 |
| 17 | 26.2 | 1771 | 18 |
| 18 | 28.2 | 1889 | 19 |

According to the present invention, polymorphic Form A of N-[4-(trifluoromethyl)benzyl]-4-methoxybutyramide may be prepared by the process comprising the following steps:

(i) reacting 4-trifluoromethylbenzylamine with methyl 4-methoxybutyrate in the presence of a catalyst thus obtaining crude N-[4-(trifluoromethyl)benzyl]-4-methoxybutyramide; and (ii) obtaining crystalline polymorphic Form A from a solution of crude N-[4-(trifluoromethyl)benzyl]-4-methoxybutyramide in an organic solvent, being said solution seeded with the polymorphic Form A of N-[4-(trifluoromethyl)benzyl]-4-methoxybutyramide.

4-trifluoromethylbenzylamine of step (i) can be prepared according to known methods of synthesis of aromatic amines. Preferably, 4-trifluoromethylbenzylamine is prepared by reacting 4-trifluoromethylbenzaldehyde with hydroxylamine according to the following scheme:

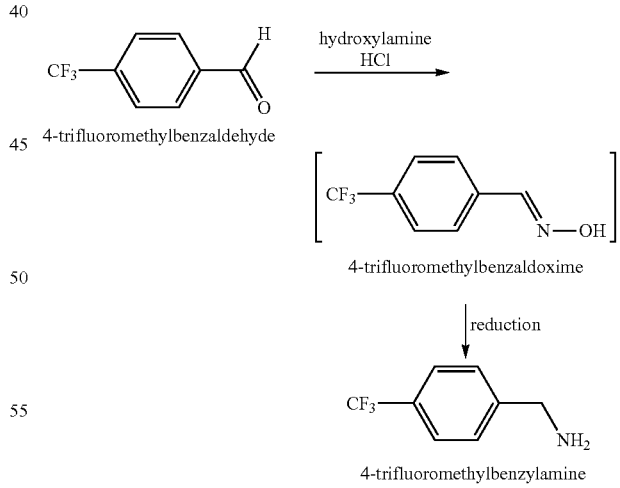

Following this scheme, the yield in 4-trifluorobenzylamine can be advantageously 90%.

According to the present invention, in the step (i), 4-trifluoromethylbenzylamine is reacted with methyl 4-methoxybutyrate in the presence of a catalyst, preferably a 30% sodium methylate solution in methanol, but N,N-dimethylaminopyridine and ammonium chloride can also be used. Preferably, such a step (i) occurs at a temperature from 95° C.

to 135° C., more preferably from 110° C. to 120° C. At the end of reaction, crude N-[4-(trifluoromethyl)benzyl]-4-methoxybutyramide can be isolated through isolation conventional techniques such as distillation with organic solvents. Advantageously, step (i) allows a yield of about 70% of crude N-[4-(trifluoromethyl)benzyl]-4-methoxybutyramide.

Crude N-[4-(trifluoromethyl)benzyl]-4-methoxybutyramide so obtained is crystallized in polymorphic Form A in step (ii) by preparing firstly a solution of crude N-[4-(trifluoromethyl)benzyl]-4-methoxybutyramide in an organic solvent and then by seeding the polymorphic Form A in said solution.

Such a solvent can be any suitable organic solvent capable to assist the crystallization of the polymorphic Form A, Preferably, such an organic solvent can be selected from toluene and a mixture of ethylacetate and n-hexane. More preferably, the solution of crude N-[4-(trifluoromethyl)benzyl]-4-methoxybutyramide is prepared with the mixture of ethylacetate:n-hexane. Advantageously, when the crude product is solubilized in the mixture of ethylacetate:n-hexane, the ratio ethylacetate:n-hexane will be from 1:4 to 1:2, more advantageously about 1:3.

The solution of crude N-[4-(trifluoromethyl)benzyl]-4-methoxybutyramide in a solvent is preferably formed by heating it from 35 and 70° C., still more preferably from 40 to 60° C. before seeding polymorphic form A. The precipitation of the polymorphic Form A occurs preferably from 0 to 35° C., more preferably from 10 to 20° C.

Advantageously, step (ii) allows a yield of about 95% of polymorphic Form A of N-[4-(trifluoromethyl)benzyl]-4-methoxybutyramide.

Figure 2:
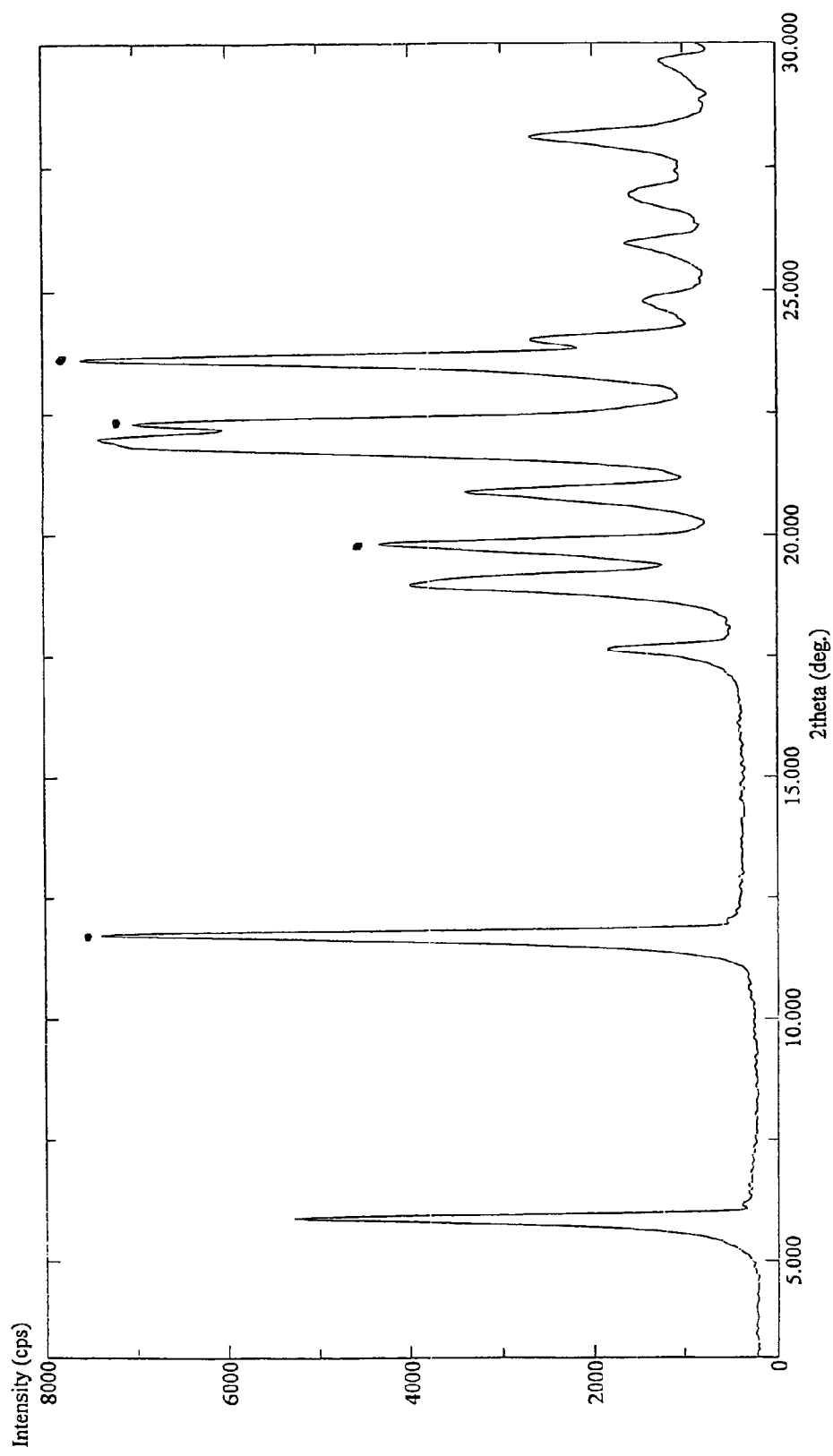
FIG. 2 shows the X-ray powder diffraction pattern of N-[4-(trifluoromethyl)benzyl]-4-methoxybutyramide in the crystalline polymorphic Form B.

According to the other embodiment of the present invention, a polymorphic Form B of N-[4-(trifluoromethyl)benzyl]-4-methoxybutyramide is provided. The polymorphic form B exhibits 16 peaks at the diffraction degrees with the intensity shown below in the Table 2 in the X-ray powder diffraction pattern as depicted in FIG. 2.

TABLE 2

Peaks of polymorphic Form B (2-theta in angular degrees ±0.2°)

| Peak | 2-theta | Intensity (cps) | I/I$_0$ |
|---|---|---|---|
| 1 | 5.9 | 5211 | 69 |
| 2 | 11.7 | 7402 | 98 |
| 3 | 17.6 | 1845 | 25 |
| 4 | 19.0 | 3985 | 53 |
| 5 | 19.8 | 4334 | 58 |
| 6 | 20.9 | 3405 | 45 |
| 7 | 21.9 | 7127 | 94 |
| 8 | 22.3 | 6896 | 91 |
| 9 | 23.6 | 7594 | 100 |
| 10 | 24.0 | 2689 | 36 |
| 11 | 24.8 | 1434 | 19 |
| 12 | 26.0 | 1654 | 22 |
| 13 | 27.0 | 1590 | 21 |
| 14 | 27.4 | 1089 | 15 |
| 15 | 28.1 | 2695 | 36 |
| 16 | 29.6 | 1252 | 17. |

According to the present invention, polymorphic Form B of N-[4-(trifluoromethyl)benzyl]-4-methoxybutyramide may be prepared by the process comprising the following steps:
i) reacting 4-trifluoromethylbenzylamine with methyl 4-methoxybutyrate in the presence of a catalyst thus obtaining crude N-[4-(trifluoromethyl)benzyl]-4-methoxybutyramide; and
(ii) obtaining crystalline polymorphic Form B from a solution of crude N-[4-(trifluoromethyl)benzyl]-4-methoxybutyramide in an organic solvent, being said solution seeded with the polymorphic Form B of N-[4-(trifluoromethyl)benzyl]-4-methoxybutyramide.

All the preferred aspects stated above for the process for preparing polymorphic Form A, namely the preparation of the benzylamine of step (i) and all the advantageous features of both step (i) and (ii), are the same for the process for preparing polymorphic Form B and here called by reference.

According to the present invention, the polymorphic Form A and polymorphic Form B are advantageously obtained by a simple process, which also avoids the use of chromatographic method in order to obtain a pure crystalline form and, more advantageously, which is reproducible and allow to obtain selectively the wished crystalline form in a stable form.

Crystalline polymorphic Forms A and B can be in particular distinguished by their X-ray powder patterns shown in FIGS. 1 and 2, respectively, but they can also be distinguished by their infrared spectra as it will be evident in the experimental parts.

Crystalline polymorphic Forms A and B are both thermodynamically stable, with no conversion of one into the other. Dissolution tests were done on each polymorph and the two Forms A and B have not shown differences in the solubility properties. They both have showed also a surprising pharmacological activity in the treatment of drug addiction and, particularly, in the treatment of alcoholism.

Owing to such properties, crystalline polymorphic Forms A and B can be used as medicaments.

Therefore, according to the present invention, a pharmaceutical composition comprising either the polymorphic Form A or the polymorphic Form B and a suitable pharmaceutically excipients is provided.

The composition according to the present invention comprises preferably from 12.5 to 50% by weight of either a polymorphic Form A or a polymorphic Form B. Such compositions may be prepared using conventional diluents or excipients and techniques known in the galenic art. The pharmaceutical compositions comprising polymorphic Forms A and B may be administered by any appropriate routes, e.g. orally or parenterally The pharmaceutical compositions for oral administration may be advantageously in the solid form, such as powders, granules, tablets, optionally effervescent, compressed or coated pills, dragees, sachets, hard or soft capsules or in the liquid form such as solutions, suspensions or emulsions. The pharmaceutical compositions for parental administration can be in the form of aqueous or nonaqueous solutions, suspensions or emulsions.

In solid compositions, the Form A or Form B may be combined with any suitable solid excipients, e.g. selected from lubricant agents, disgregating agents, fillers and so on.

In liquid compositions, the Form A or Form B can be, for example, dissolved in water, organic solvents or alcohols.

Polymorphic Form A and polymorphic Form B can be advantageously used in the treatment of drug addiction and in the treatment of alcoholism.

For these aims, the polymorphs can be preferably administered in doses from 5 to 50 mg/kg.

Even if both the polymorphs have similar features and similar activities in order to be used as medicaments, according to the present invention, polymorphic Form A of N-[4-(trifluoromethyl)benzyl]-4-methoxybutyramide is preferred. As a matter of facts, such a polymorphic Form A has showed optimal physical properties, such as compressibility and density, thus resulting in better workability and handling, which are extremely important in formulation and product manufacturing.

Furthermore and as it will be evident from the experimental part, polymorphic Form A surprisingly has shown therapeutic activity on alcohol dependence even is at very low pharmacological doses from 5 to 10 mg/Kg.

Form A was also tested for safety pharmacology, toxicology and genotoxicity and it resulted as being safe with a very low toxicity and genotoxicity profiles as demonstrated below.

The invention will now described in greater details by way of non-limiting examples in order to better characterize both Form A and Form B and their chemical-physical and pharmacological features.

EXAMPLE 1

Preparation of Polymorphic Form A of N-[4-(trifluoromethyl)benzyl]-4-methoxybutyramide A) Preparation of 4-Trifluoromethylbenzylamine In a reactor 15 Kg of distillate water, 2.50 Kg of sodium acetate, 2.30 Kg of hydroxylamine hydrochloride, 4.00 Kg of methanol were charged. At room temperature, 5.0 Kg of trifluoromethylbenzaldehyde were added and the mixture was firstly stirred for about thirty minutes and then 5 Kg of solvent were distilled under vacuum. 12.0 Kg of 80% acetic acid was then added and then 4.5 kg of zinc were added in portions, thus letting the temperature rise until 60-80° C. by exothermicity. Such a temperature was then maintained by cooling. At the end of the reaction, 10.0 Kg of toluene and 15.0 kg of 30% ammonia were added to remove zinc salts. The mass so obtained was stirred at 50-60° C. and the lower aqueous phase was then discarded.

After distillation under vacuum until about half volume, the toluenic solution containing 4-trifluoromethylbenzylamine was recovered and used in the subsequent step (i).

4.00 kg of 4-trifluoromethylbenzylamine were obtained as determined by potentiometric titration. Yield: 79.5%

B) Step i) of Preparation of Crude N-[4-(trifluoromethyl)benzyl]-4-methoxybutyramide The toluenic solution obtained in A) (4.00 Kg of 4-trifluoromethylbenzylamine) was charged in a reactor. After distillation until an oil residue was obtained, 3.20 Kg of methyl 4-methoxybutyrate, 0.40 kg of 30% sodium methylate were added. The solution was then heated to 110-120° C., distilling at atmospheric pressure in order to remove all methanol (also methanol freeing from the reaction) and maintaining such temperature for at lest two hours. The reactor at 110-120° C. was then put under vacuum for at least one hour. At the end of the reaction, 12.0 Kg of toluene, 2.0 Kg of water and 0.40 Kg of 80% acetic acid were added to the mass. After stirring, the lower aqueous phase was separated and removed. The organic phase was then distilled under vacuum to a oil residue. To such a residue, 4.00 Kg of ethylacetate, 12.0 Kg of n-hexane were added and the final mass was heated to 40-60° C. until a complete solution was obtained. Then the solution was brought to 20-30° C. and so maintained until a good precipitation was obtained. The mass was then cooled to 0° C.-10° C., centrifuged by washing with a mixture of 0.80 Kg of ethylacetate, 4.00 Kg of n-hexane. The obtained humid product was used as such in the following step.

About 3.8 Kg of crude N-[4-(trifluoromethyl)benzyl]-4-methoxybutyramide were obtained. Yield: 60.5%

C) Step (ii) of Crystallization of Polymorphic Form A of N-[4-(trifluoromethyl)benzyl]-4-methoxybutyramide In a reactor 3.8 Kg of crude N-[4-(trifluoromethyl)benzyl]-4-methoxybutyramide (the correspondent humid product), 3.8 Kg of ethylacetate and 11.4 Kg of n-hexane were charged. The mass was heated to 40-60° C. until a complete solution was obtained and the solution was then brought to 25-35° C. 0.038 Kg of polymorphic Form A of N-[4-(trifluoromethyl)benzyl]-4-methoxybutyramide were seeded. The mass was maintained at 25-35° C. for at least one hour and then cooled to 10-20° C. and again maintained for at least one hour. The mass was then centrifuged, by washing with a mixture previously prepared and containing 0.76 Kg of ethyl acetate, 2.28 Kg of n-hexane. The obtained product was dried at 40-50° C. About 3.4 Kg of polymorphic Form A of N-[4-(trifluoromethyl)benzyl]-4-methoxy butyramide were obtained. Yield: 89.5%

EXAMPLE 2

Preparation of Polymorphic Form B of N-[4-(trifluoromethyl)benzyl]-4-methoxybutyramide Following the same procedure and using the same amounts of experimental parts A) and B) of example 1) crude N-[4-(trifluoromethyl)benzyl]-4-methoxybutyramide was obtained.

C) Step (ii) of Crystallization of Polymorphic Form B of N-[4-(trifluoromethyl)benzyl]-4-methoxybutyramide In a laboratory flask 34.0 g of N-[4-(trifluoromethyl)benzyl]-4-methoxy butyramide, 34.0 g of ethylacetate, 102 g of n-hexane were charged. The mass was then heated to 40-60° C. until a complete solution was obtained. The solution was hence cooled to 25-35° C. and 0.35 g of polymorphic Form B of N-[4-(trifluoromethyl)benzyl]-4-methoxybutyramide were seeded. The mass was maintained at 25-35° C. for at least one hour and then cooled to 10-20° C. and again maintained for at least one hour. The mass was then centrifuged, by washing with a mixture previously prepared and containing 6.8 g of ethyl acetate and 20.4 g of n-hexane. The obtained product was dried at 40-50° C. About 31 g of polymorphic Form B of N-[4-(trifluoromethyl)benzyl]-4-methoxybutyramide were obtained.

EXAMPLE 3

Analysis of Polymorphic Form A of N-[4-(trifluoromethyl)benzyl]-4-methoxybutyramide Firstly, the crystallized product of Example 1 was analysed in order to confirm it was N-[4-(trifluoromethyl)benzyl]-4-methoxybutyramide.

A sample of Example 1 was subjected to:

MASS analysis through (+)ESI (Electro-Spray Ionization) technique with Thermo-Finnigam LCQ-Advantage Instrument.

The Molecular Weight resulted to be 275, while from mass/mass fragmentation pattern, the results were as in the following Table 3:

TABLE 3

Results from mass/mass fragmentation pattern

| m/z | Assignment |
| --- | --- |
| 276 | [M + H]+ |
| 244 | [structure: 4-(trifluoromethyl)benzyl but-3-enamide cation] + H |

The molecular weight and mass/mass fragmentation pattern confirmed the structure of N-[4-(trifluoromethyl)benzyl]-4-methoxybutyramide.

$^1$H-NMR analysis through $CDCl_3$ and $CDCl_3+D_2O$ solvent with Variant Geminy 200 Instrument operating at 200 MHz The NMR spectrum confirmed the structure of N-[4-(trifluoromethyl)benzyl]-4-methoxybutyramide according to the following results:

TABLE 4

$^1$H-NMR spectrum of N-[4-(trifluoromethyl)benzyl]-4-methoxybutyramide

| δ (ppm) | multiplicity | (H) | J(Hz) | Assignment |
| --- | --- | --- | --- | --- |
| 1.91 | d-triplet | (2) | 6.2; 7.3 | $CH_2$ |
| 2.33 | triplet | (2) | 7.3 | $CH_2$ |
| 3.28 | singlet | (3) | — | $CH_3$ |
| 3.40 | triplet | (2) | 6.2 | $CH_2$ |
| 4.46 | doublet | (2) | 5.9 | $CH_2$ |
| 6.31 | broad singlet | (1) | — | NH |
| 7.37 | AA'BB 'System | (2) | 8.1 | H; H |
| 7.56 | AA'BB 'System | (2) | 8.1 | H; H |

Elemental Analysis

The sample gave the following elemental values, which corresponded to the calculated ones:

TABLE 5

Elemental values for $C_{13}H_{16}NO_2F_3$

| | Calculated (%) for $C_{13}H_{16}NO_2F_3$ | Found (%) |
| --- | --- | --- |
| C | 56.72 | 56.52 |
| H | 5.82 | 5.87 |
| N | 5.09 | 5.00 |
| O | 11.64 | 11.33 |
| F | 20.73 | 20.48 |

EXAMPLE 4

Analysis of Polymorphic Form B of
N-[4-(trifluoromethyl)benzyl]-4-methoxybutyramide The mass, 1H-NMR and elemental analyses were repeated with a sample of the crystallized product obtained according to Example 2, by using the same techniques and instruments. All the retrieved data confirmed that the product of Example 2 was N-[4-(trifluoromethyl)benzyl]-4-methoxybutyramide.

EXAMPLE 5

Determination of the Polymorphism of
N-[4-(trifluoromethyl)benzyl]-4-methoxybutyramide Two samples of crystallized products of Examples 1 and 2 were analyzed through:
  X-ray powder diffraction with Rigaku Miniflex Instrument and using Cu-$α_1$-radiation and Cu-$α_2$-radiation;
  DSC analysis with Perkin-Elmer DSC 6 Instrument and using a scanning rate of 10° C./min in a range of temperature of 50-260° C.;
  Infrared analysis with Perkin-Elmer FT-IR Spectrum-one, wherein the analysed sample is a suspension in KBr.

The X-ray powder diffraction pattern of a sample of polymorphic Form A of Example 1 is shown in FIG. 1 and all 2-theta and Intensity (cps) values are in the above Table 1.

The X-ray powder diffraction pattern of a sample of polymorphic Form B of Example 2 is shown in FIG. 1 and all 2-theta and Intensity (cps) values are in the above Table 2.

Figure 3:
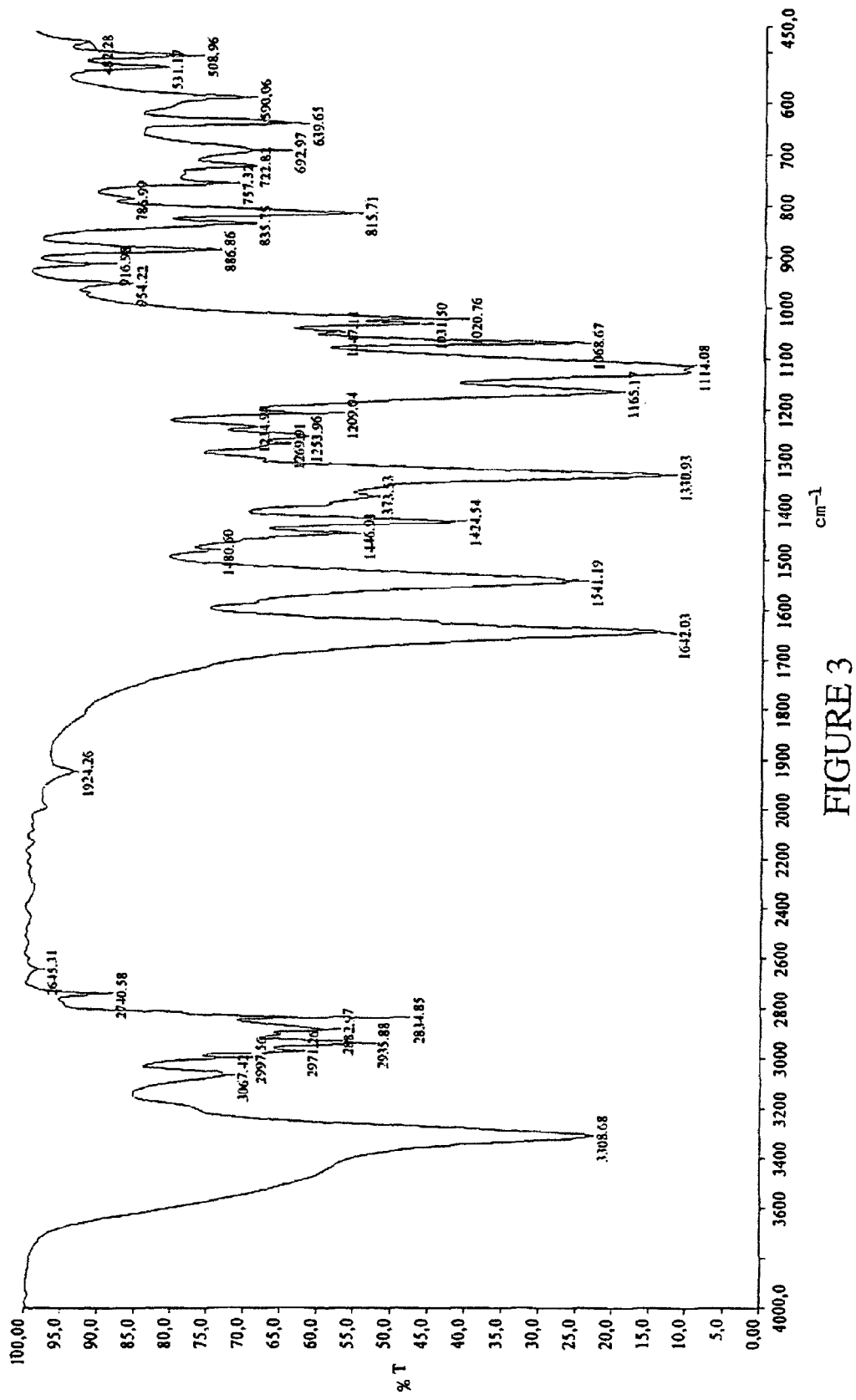
FIG. 3 shows the infrared spectrum of crystalline polymorphic Form A of N-[4-(trifluoromethyl)benzyl]-4-methoxybutyramide.

The IR spectrum of polymorphic Form A (Example 1) is shown in FIG. 3. The IR bands ($cm^{-1}$), as depicted in FIG. 3 are the following: 3308.68, 3067.42, 2997.56, 2971.26, 2935.88, 2882.97, 2834.85, 2740.58, 1924.26, 1642.03, 1541.19, 1480.60, 1446.91, 1424.54, 1373.53, 1330.93, 1253.96, 1234.94, 1209.04, 1165.17, 1114.08, 1068.67, 1047.11, 1031.50, 1020.76, 954.22, 916.98, 886.86, 835.75, 815.71, 757.32, 722.82, 692.97, 639.65, 590.06, 531.17, 508.96, 482.28.

Figure 4:
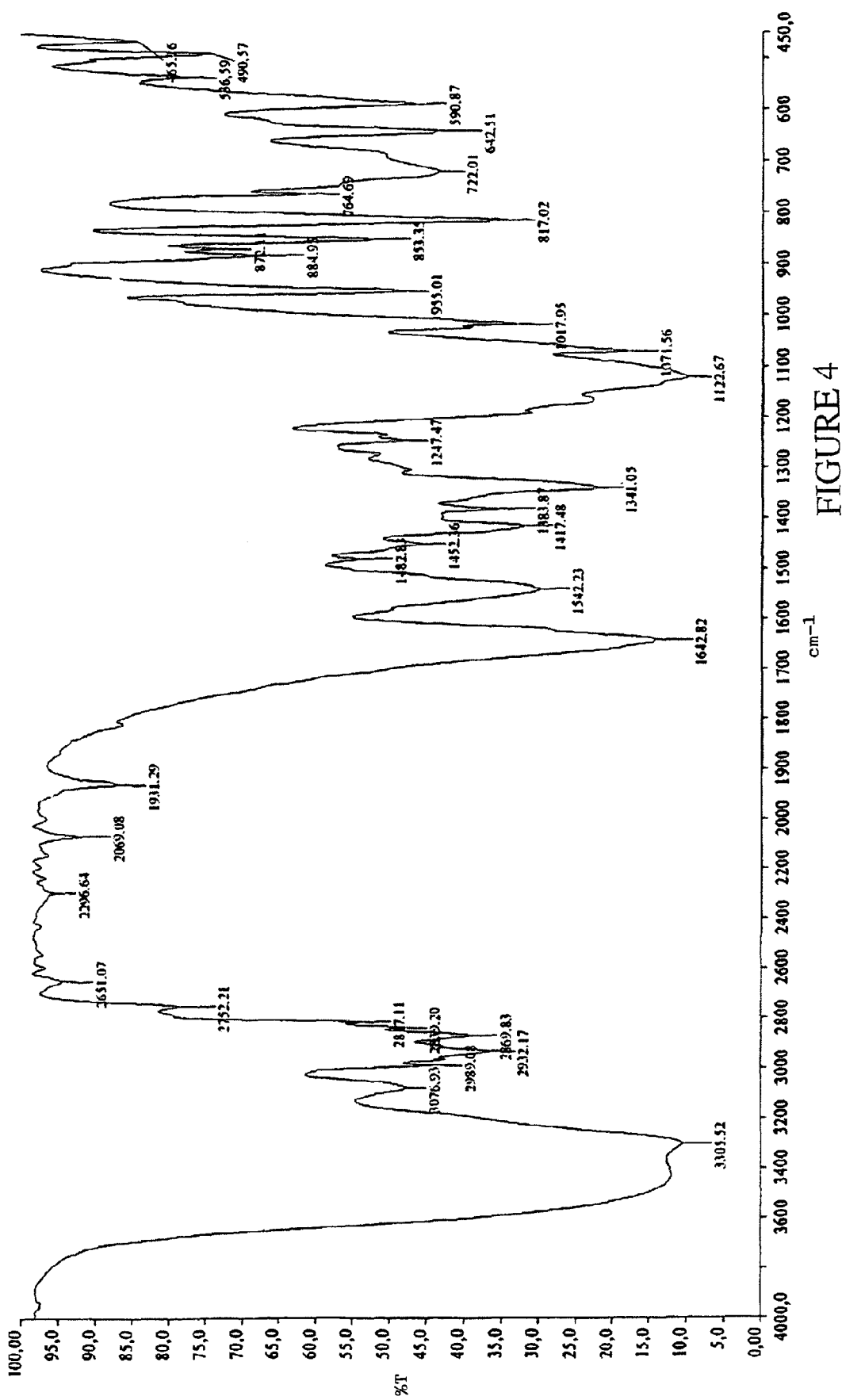
FIG. 4 shows the infrared spectrum of crystalline polymorphic Form B of N-[4-(trifluoromethyl)benzyl]-4-methoxybutyramide.

The IR spectrum of polymorphic Form B (Example 2) is shown in FIG. 4. The IR bands ($cm^{-1}$), as depicted in FIG. 4 are the following: 3305.52, 3076.93, 2989.08, 2932.17, 2869.83, 2839.20, 2817.11, 2752.21, 2651.07, 2296.64, 2069.08, 1931.29, 1642.82, 1542.23, 1482.83, 1452.36, 1417.48, 1383.87, 1341.05, 1247.47, 1122.67, 1071.56, 1017.95, 955.01, 884.95, 872.11, 853.35, 817.02, 764.69, 722.01, 642.51, 590.87, 536.59, 490.57, 465.16.

Figure 5:
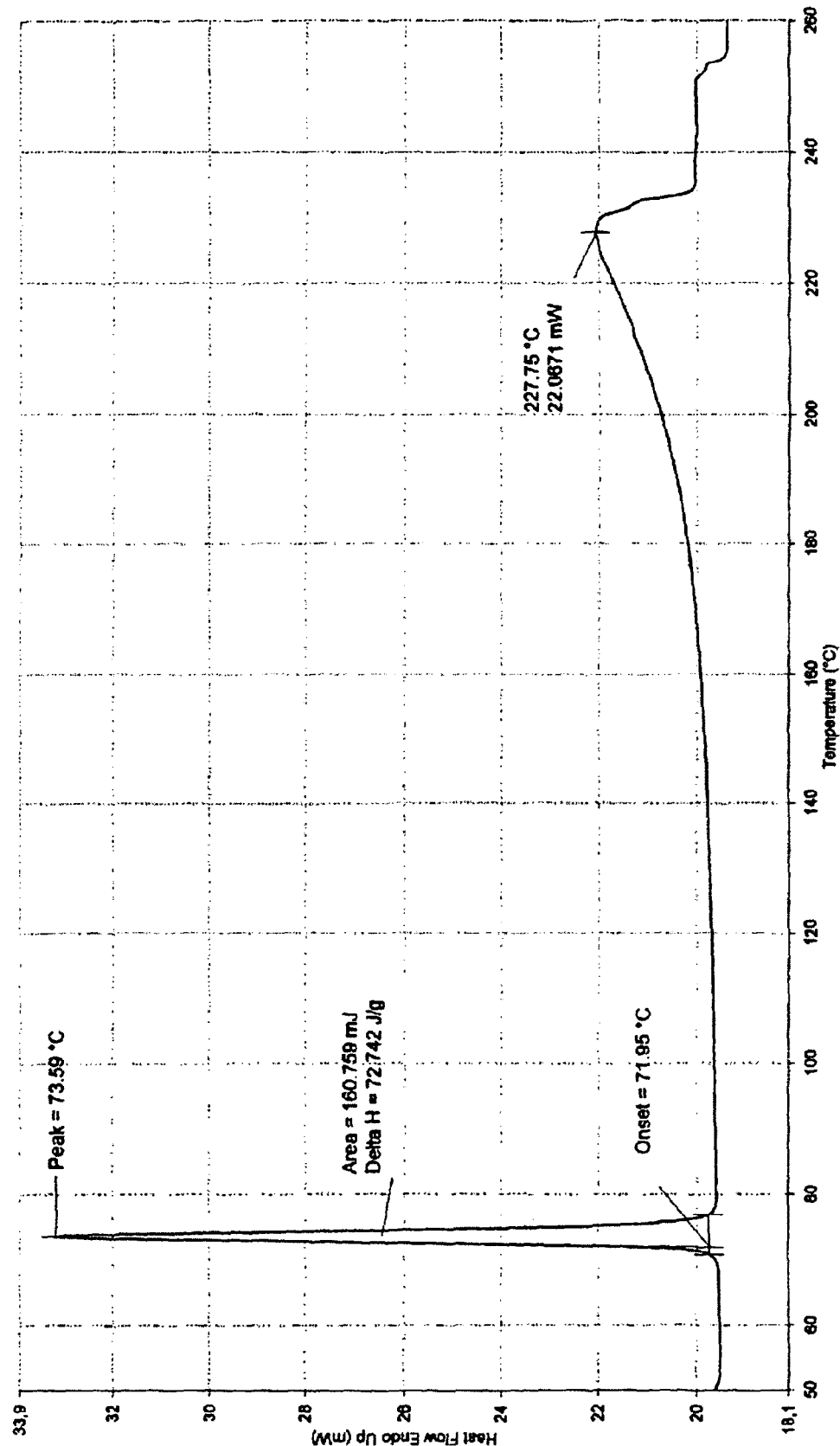
FIG. 5 shows the Differential Scanning Calorimetric (DSC) spectrum of polymorphic Form A of N-[4-(trifluoromethyl)benzyl]-4-methoxybutyramide.
Figure 6:
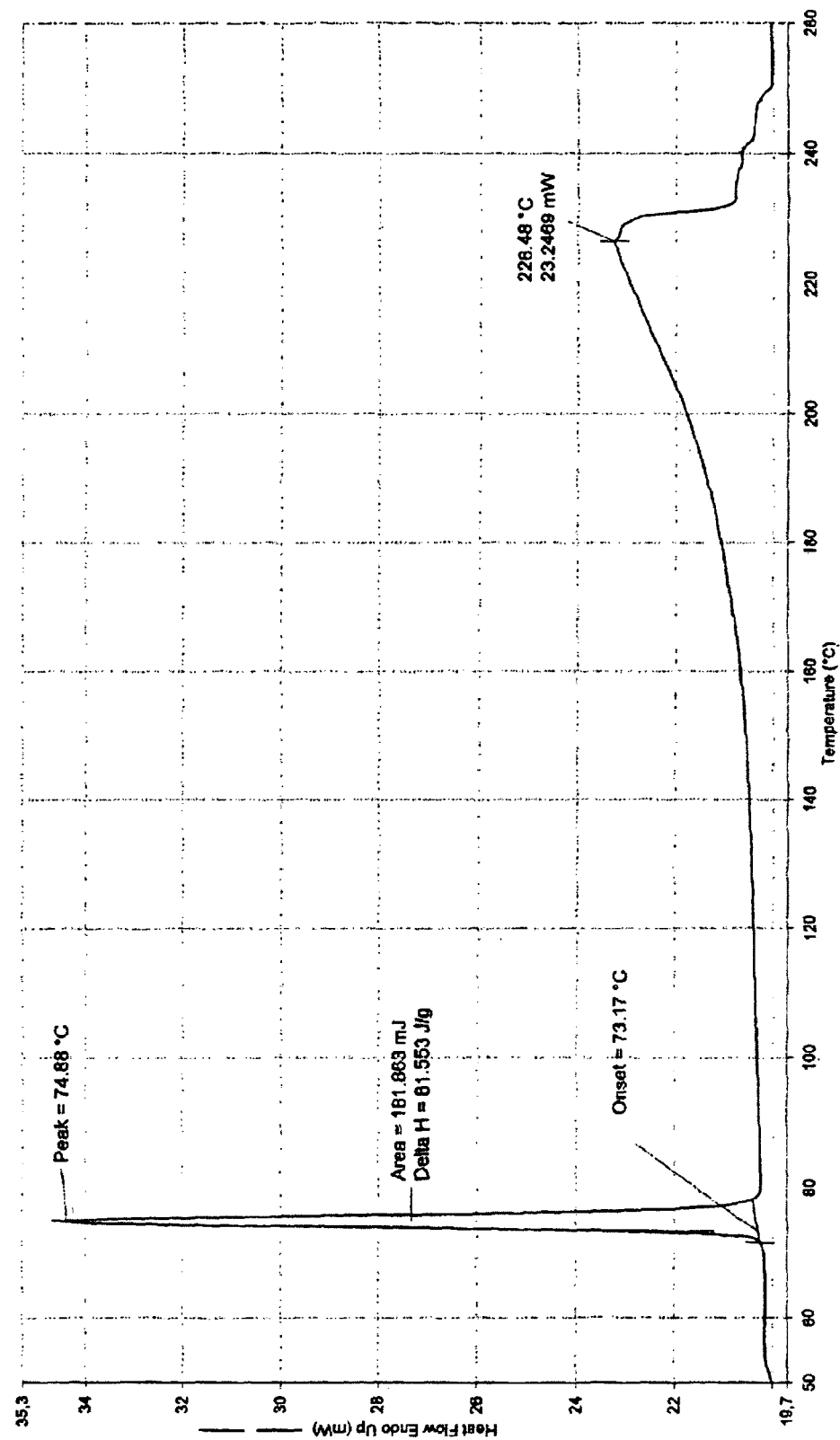
FIG. 6 shows the Differential Scanning Calorimetric (DSC) spectrum of polymorphic Form B of N-[4-(trifluoromethyl)benzyl]-4-methoxybutyramide.

The DSC spectra for polymorphic Form A (as obtained from Example 1) and polymorphic Form B (as obtained from Example 2) are shown in FIGS. 5 and 6, respectively, on which onset temperatures and peak temperatures are indicated. From all FIGS. 1-6, it is evident that Form A and Form B both consist of isomorph crystals. However, on the basis of retrieved values in the different analyses, Polymorphic Form A and polymorphic Form B have different crystalline structure.

Figure 7:
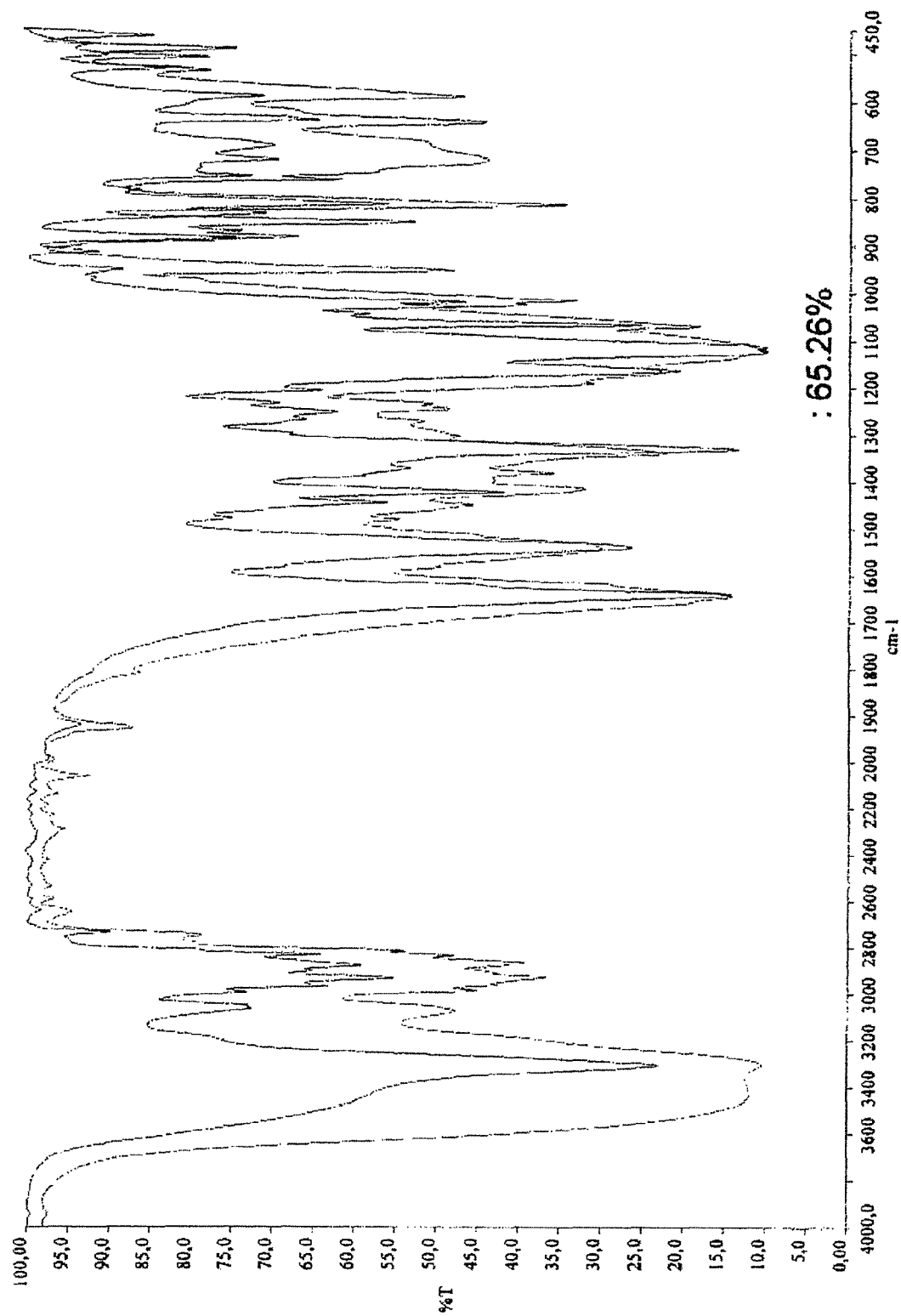
FIG. 7 shows the correlation between the IR spectrum of polymorphic Form A and polymorphic Form B of N-[4-(trifluoromethyl)benzyl]-4-methoxybutyramide.

In order to better underline the differences in structure, the IR spectrum of Example 1 sample (Form A) as depicted in FIG. 3 and IR spectrum of Example 2 sample (Form A) as depicted in FIG. 4 were overlapped as represented in FIG. 7 and their correlation was calculated. The correlation value was 65.26%. This result and FIG. 7 confirmed that Form A and Form B were two distinct polymorphs of N-[4-(trifluoromethyl)benzyl]-4-methoxybutyramide.

EXAMPLE 6

Evaluation of Physical-Chemical Characteristics of a
Sample of Polymorphic Form A and a Sample of
Polymorphic Form B A sample of polymorphic Form A obtained as in Example 1 and then micronized less than 10 microns was analysed.

The results of the analysis are given in the following Table 6.

TABLE 6

Physical-chemical characteristics of polymorphic Form A and Form B

|  | Polymorphic Form A | Polymorphic Form B |
|---|---|---|
| Description | crystalline white powder | white powder (lightly sticky and waxy) |
| Melting point (° C.) | 73.2° C. | 73.4 |
| Water (KF titration) (%) | less than 0.01 | 0.01 |
| Assay (volumetric, on anhydrous basis) (%) | 99.5 | 100 |
| Chromatographic purity (%) | 0.05 | 0.04 |

The two polymorphs appeared to be crystalline, with high purity. Furthermore, polymorphic Form A appeared as an entirely crystalline powder. Owing to this feature, from which better workability and handling can be derived, polymorphic Form A was judged the best candidate for preparing pharmaceutical compositions.

Both samples of powder (Form A and Form B) were used in order to evaluate the solubility properties of the two polymorphs at different pH.

The two samples were tested in the following pH conditions:

Hydrochloric acid buffer at pH=1.2
Acetic acid at pH=3.0
Phosphate buffer at pH=3.0
Phosphate buffer at pH=4.6
Phosphate buffer at pH=6.0
Phosphate buffer at pH=7.4
Alkaline phosphate buffer at pH=8.0

0.5 g of each samples were dissolved in a glass flask using 100 ml of the appropriate buffer. The two samples were then kept under stirring for 30 minutes. If the samples were completed dissolved, 1 additional gram was added in the flask and stirred for 30 minutes. The procedure was repeated till the presence of undissolved product in the bottom of the flask. After such a dissolution procedure, the samples were stored for 24 hours and then the dissolved amounts of Form A and Form B, respectively, were determined by HPLC assay. The results are in the following Table 7:

TABLE 7

Solubility of polymorphic Form A and polymorphic Form B at different pH

|  | Polymorphic Form A Solubility (µg/ml) | | Polymorphic Form B Solubility (µg/ml) | |
|---|---|---|---|---|
| pH | Initial evaluation | After 24 hours | Initial evaluation | After 24 hours |
| 1.2 | 152.58 | 159.79 | 136.12 | 164.47 |
| 3.0 (acetic acid) | 123.88 | 160.12 | 143.69 | 164.84 |
| 3.0(phosphate buffer) | 116.50 | 150.75 | 126.87 | 156.73 |
| 4.6 | 132.41 | 145.44 | 129.35 | 147.14 |
| 6.0 | 118.44 | 139.92 | 125.95 | 143.2 |
| 6.8 | 106.03 | 164.22 | 131.46 | 146.25 |
| 7.4 | 117.16 | 139.97 | 113.60 | 143.79 |
| 8.0 | 133.86 | 141.89 | 130.61 | 146.25 |
| Water | 137.80 | 164.19 | 125.44 | 162.64 |

The two polymorphs did not show peculiar differences in the dissolution properties.

The solubility of both compounds was not affected by pH and also in this case the minimal differences were not significant. The solubilities were low, confirming the high stability of the two polymorphs. After 24 hours the solubility increased of 10-30% in the different pH conditions. According to this test, both Form A and Form B can be used for preparing medicaments.

EXAMPLE 7

Pharmacological Tests

A) Evaluation of Polymorphic Form A of N-[4-(trifluoromethyl)benzyl]-4-methoxybutyramide in the Treatment of Alcohol Dependence.

Tests were carried out in Sardinian Alcohol preferring rats (sP), i.e. a rodent line genetically selected for their spontaneous alcohol consume. These animals were adopted as the main specific animal model in the research program due to the fact that these rats (kept in a free-choice regimen between water and a 10% ethanol solution) consume large amounts of alcohol (6-7 g/Kg/day), sharing a great preference for the tested compound (80-100%).

Under the standard, these rats are subjected to homecage two-bottle free choice regimen between 10% alcohol and water with unlimited access (24 h/day) and they show these features: daily intake of about 6 g/Kg of alcohol; preference ratio (alcohol solution vs total fluids) above 80%; fractioning of daily alcohol intake in 3-4 binges; achievement of BALs (Blood Alcohol Levels) above 50 mg % at each binge; induction of pharmaceutical effects (anxiolysis, motor stimulation) and regulation by a central, hedonic set-point mechanism.

The tests were carried out according to the following models:

1. Spontaneous alcohol intake in non deprived sP rats
2. Alcohol Deprivation Effect in deprived sP rats.

1. Spontaneous Alcohol Intake in Non Deprived sP Rats

According to this model, the alcohol intake in a two bottles free-choice regimen represents the "active drinking" phase of human alcoholism. Therefore the tested active compounds should decrease the propension of rats to consume alcohol. Comprehensive results in this model demonstrated that polymorphic Form A decreases the alcohol intake in a wide range of doses (10-100 mg/kg) after intragastric acute administration. It is important to underline that the antialcohol effect was specific, that is the decrease of alcohol intake was not related to sedative effect, as demonstrated by the compensatory increase of water intake and by the normal food intake in sP rats (data not reported). In FIG. 8A the results of a single experiment are shown. Specifically 10, 20, 25 and 50 mg/kg doses of polymorphic Form A were administered and the alcohol intake was evaluated. Surprisingly, doses as low as 10 mg/kg significantly reduced alcohol intake.

2. Alcohol Deprivation Effect in Deprived sP Rats

To further characterize the anti-alcohol effect of polymorphic Form A, this compound was evaluated on the Alcohol Deprivation Effect (ADE). ADE is a well documented temporary increase of alcohol intake that occurs after a period of abstinence and a model for the compulsive, uncontrolled alcohol seeking and taking behaviour which characterizes alcohol relapses in alcoholics. According to this model, alcohol experienced sP rats underwent a two weeks period of abstinence during which there was no access to ethanol. After this period, the animals were administered with polymorphic Form A 30 min before lights off, and then re-accessed to alcohol. Intake was measured 1 hour after lights off.

The results are depicted in FIGS. 8B and 8C for high doses and low doses of crystalline polymorphic Form A, respectively. Polymorphic form A completely suppressed ADE effect showing a very good activity in a dose range of 5-100 mg/Kg. Moreover, doses as low as 5 mg/Kg were capable to completely abolish the extra-consume of alcohol.

EXAMPLE 8

Evaluation of Safety Pharmacology, Toxicology and Genotoxicity of Polymorphic Form A 1. Safety Pharmacology The possible adverse effects of polymorphic Form A on the CNS, cardiovascular, respiratory and immune functions were evaluated in vitro and in vivo (rats and dogs) in different experimental models. In the in vivo tests, the tested compound was always given by single oral administration at the doses of 100, 300 and 1000 mg/kg.

A) CNS System

Irwin's Test and Body Temperature in Rats

Neurobehavioural effects of polymorphic Form A have been investigated according to the Irwin Test by using a standard observation battery, which allows the assessment of both peripheral and central nervous system activities (e.g. motor activity, motor co-ordination, somatic sensory/motor reflex responses, autonomic responses); body temperature was measured by means of an electronic thermometer. The compound induced at 100 mg/kg a transient decrease in spontaneous locomotor activity; at the higher doses the effect on locomotion was more marked and more long lasting and associated to a miorelaxant effect and to a decrease in awareness. At 1000 mg/kg rats showed a tip toe position, ataxic and subsequently a lying recumbent or flattened position; all the effects were reversible. The body temperature was not affected at 100 mg/kg, while at the higher doses a significant decrease in body temperature was seen up to four hours.

Hexobarbital Sleeping Time in Rats

The test consists in the measurement of the duration of hexobarbital-induced sleep; substances with a sedative or antisleep action cause increase or decrease respectively in the duration of hexobarbital induced sleep. No statistical significant effect on the time taken to fall asleep or on the duration of the sleep was seen at the lowest dose (100 mg/kg). At the intermediate dose a slight decrease in sleep duration was recorded, while at the highest dose a significant decrease of the time taken to fall asleep and of the duration of the sleep were observed.

Proconvulsant Activity in Rats

In the study it was investigated a possible proconvulsant effect of polymorphic Form A administered in combination with a dose of pentylenetetrazol, that induced seizures; pre-treatment with substances which possess proconvulsant properties led to a more rapid onset of seizures. At all the doses administered, polymorphic Form A had no statistical significant proconvulsant effect, while at the doses at 100 and 300 mg/kg induced an increase in the time of occurrence of seizures suggesting a possible anticonvulsant effect.

B) Cardiovascular Apparatus

In Vitro

HERG Cells (Human Ether Related Gene Cells)

A possible blocking effect of polymorphic Form A on Herg tail current recorded from HEK-293 cells (Human Embryonic Kidney cells) stably transfected with HERGG-1 cDNA was investigated. The method consisted in measuring the HERG tail current by using the patch clamp techniques in the whole cell configuration. Compounds which inhibited HERG current were recognized to prolong the cardiac action potential and increase QT interval.

The obtained results indicated that polymorphic Form A induced no statistically significant inhibition of HERG tail current at $10^{-7}$ M; at the concentrations of $10^{-6}$ and $10^{-5}$ M, a slight and non dose-dependent decrease was observed and only at the highest concentration tested $10^{-4}$ M a reduction of about 50% occurred. It is to underline that the inhibition never reached the value of 70%, that it is considered the threshold value to consider a compound active in this test.

Purkinje Fibres

A possible adverse effect induced by polymorphic Form A on cardiac action potential was evaluated in isolated canine Purkinje fibres. Transmembrane action potential was measured by means of the intracellular microelectrode technique; this method is recommended to detect the capacity of a substance to induce prolongation of the QT interval. Polymorphic Form A at concentrations of $10^{-7}$, $10^{-6}$ and $10^{-5}$ M had no statistically significant effect on action potential parameters under either normal or low stimulation rates; at the very high concentration of $10^{-4}$ M a significant decrease in action potential duration of repolarisation was observed. At all the concentrations tested neither early nor delayed after-depolarisation were recorded.

These results indicated that, on the basis of the electrophysiological profile of polymorphic Form A, no TDP (Torsade de Pointes) or QT prolongation are to be expected; polymorphic Form A can be classified among the drugs capable to not induce TDP or QT prolongation in humans.

In Vivo

Cardiovascular Evaluation in Conscious Dogs

Any possible effect of polymorphic Form A administered at the doses of 100, 300 and 1000 mg/kg by oral route on blood pressure, heart rate and electrocardiogram was evaluated in conscious dogs, free to move about, previously instrumented with telemetric transmitters. In the first part of the study, only telemetric measurements were recorded; the recording of the parameters started at least 24 hours before the administration of the compound and were continued for 24 hours following dosing. In the second part, only the highest dose of 1000 mg/kg was administered and complementary investigations such as 6-lead electrocardiogram (leads I, II, III, aVL, aVR and aVF), blood sampling and observation of the animals were performed before treatment and 3 hours post-treatment.

First Part: Polymorphic Form A given at 100 mg/kg did not induce relevant changes of blood pressure, heart rate and electrocardiogram tracing (in particular no change in T wave morphology). When given at 300 and 1000 mg/kg a slight increase in arterial blood pressure (mean, systolic and diastolic arterial pressure), a slight decrease in PR and PQ interval durations and a slight increase in QT interval duration corrected for heart rate with the Sarma's method were recorded. Changes observed at 300 mg/kg were very slight and isolated and were consequently not attributable to a pharmacologically relevant effect of polymorphic Form A as the changes in PR and PQ interval duration observed at 1000 mg/kg, while the increase in QT interval duration corrected for heart rate were clearly related to an effect of polymorphic Form A, suggesting an increase in the duration of ventricular repolarisation. No disturbance in the electrocardiogram (lead II) and, in particular, no change in T wave morphology was observed at all the doses tested.

Second Part: No disturbance in the 6-lead electrocardiogram was observed before and 3 hours after dosing with polymorphic Form A at the dose of 1000 mg/kg. All animals vomited between 0.5 and 17 hours after dosing. Plasma analysis confirmed the presence of polymorphic Form A in plasma 3 hours after the administration.

These results indicate that polymorphic Form A, administered at the doses of 100, 300 and 1000 mg/kg by the oral route induced only at 1000 mg/kg a slight hypertension associated to an increase in the duration of ventricular repolarisation.

C) Respiratory System

Respiratory Evaluation in Conscious Rats

The effect of polymorphic Form A on respiratory parameters (respiratory rate, peak inspiratory and peak expiratory flows, inspiration and expiration times, airway resistance index, minute volume and tidal volume) was assessed in conscious rats after single oral administration. Respiration was measured by the whole body plethysmography method. Polymorphic Form A at 100 mg/kg had no relevant effect on respiratory parameters, at 300 and 1000 mg/kg induced tachypnoea associated to a transient reduction in tidal volume. No statistically change was observed in peak inspiratory and peak expiratory flows, minute volume or airway resistance index, suggesting that the test compound did not cause any respiratory depressant or bronchoconstrictor effect.

D) Immune System

PCF Test in Rats

A possible effect of polymorphic Form A on the immune system was evaluated by using the method system of Plaque Forming Cells (PCF) in the rat, following oral administration to rats for 28 days at the doses of 150, 250 and 500 mg/kg. The method is based on the stimulation of the immune system with an antigenic agent (sheep's red blood cells) and on the evaluation of the effect of the test item on the immune response. The immune response was assessed by measuring the proportion of splenocytes which produced antibodies against the antigenic agent (Plaque Forming Cells) in presence of complement. The results obtained in the study showed that polymorphic Form A had a slight and not dose-dependent immunosuppressant activity; at the lower doses tested (150 and 250 mg/kg) there is a comparable borderline effect that only at the highest dose (500 mg/kg) becomes clear-cut. In fact, statistical analysis evidenced a significativity at 150 mg/kg, but not at 250 mg/kg; these findings might indicate that the effects is observed at these doses could be due to the variability normally present in this test as heterogeneity in immune response is often seen and it is likely to be related to individual differences in immune sensitivity, All the above mentioned studies for safety pharmacology have been conducted following GLP regulations and in compliance with ICH S7A guideline for Safety Pharmacology.

2. Toxicology and Genotoxicity

Single and repeated-dose toxicity studies in rodents and non-rodents were carried out to support the clinical trials of the test compound, i.e. polymorphic Form A. Single toxicity studies were performed in mice and rats by the intraperitoneal and the oral routes. Repeated oral studies (28 days administration followed by 14 days recovery period) were performed in rats and dogs.

Ames and Micronucleus test were carried out to investigate the compound's genotoxic potential.

The following Table 8 summarized the studies conducted with polymorphic Form A.

TABLE 8

Toxicity and genotoxicity studies of polymorphic Form A.

| Study type | Species | Route | Dose-range (mg/kg) | Schedule | Results |
|---|---|---|---|---|---|
| Acute Toxicity | Mouse | ip os | 200-1000 2000-4000 | Single | $LD_{50} \sim 800$ $LD_{50} > 4000$ |
| Acute Toxicity | Rat | Ip os | 200-1000 2000-4000 | Single | $LD_{50} \sim 800$ $LD_{50} > 4000$ |
| Subchronic Toxicity | Rat | os | 50-1550/1200 | 4 week + recovery | NOEL* 100 |
| Subchronic Toxicity | Dog | os | 125-1125/900 | 4 week + recovery | NOEL* 125 |
| Genotoxicity Ames test | S. typhimurium | In vitro | 3-500 µg/ml | / | Negative |
| Micronucleus Test | Rat (Bone marrow Cells) | os | 500-2000 | Single | Negative |

*NOEL: No Observable Effects Level

Genotoxicity was Evaluated with Ames Test and Micronucleus Test in the Rat

Salmonella Typhimurium Reverse Mutation Assay (Ames Test)

The mutagenic potential of polymorphic Form A was evaluated in vitro in the Salmonella Typhimurium Reverse Mutation Assay according to EC guidelines. The compound tested did not induce gene mutations by base pair changes or frameshifts in the genoma of the strains of Salmonella typhimurium tested (TA 1535, TA 1537, TA 98, TA 100 and TA102) at concentrations ranging from 50 to 3000 µg/ml with and without metabolic activation. Therefore polymorphic Form A is to be considered non-mutagenic in this Salmonella typhimurium reverse mutation assay.

Micronucleus Test

Any clastogenic or spindle poison activity of polymorphic Form A was investigated by detecting micronucleated polychromatic erythrocytes in the bone marrow of treated rats. The study was conducted in compliance with the EC Guidelines. The method involved searching for the presence of a chromosome fragment, or a number of chromosomes, resulting from a deletion or a mitotic spindle poison effect, in the polychromatic erythrocytes in the bone marrow. Clastogenic products may produce, at the moment of mitosis, chromosome breakage, while spindle poisons disturb the structure of the mitotic spindles. An acentric fragment of a chromosome that has not migrated normally is not retained in the nucleus of the daughter cell, and appears in the cytoplasm. It is then known as a Howell-Jolly body or micronucleus. The micronucleus can be detected in polychromatic erythrocytes, as these cells expel their main nucleus shortly after the last mitosis and the micronucleus remains in the red blood cells. Male and female Sprague Dawley rats were treated orally once with 2000-1000-500 mg/kg of polymorphic Form A and 24 and 48 hours after the treatment their femurs were sampled and bone marrow cells were extracted.

At all the doses and the times tested polymorphic Form A induced no clastogenic activity.

The invention claimed is:

1. Polymorphic Form A of N-[4-(trifluoromethyl)benzyl]-4-methoxybutyramide of formula:

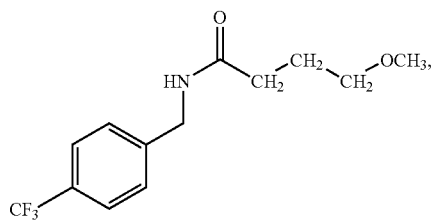

(I)

having the following peaks at the diffraction degrees (2-theta) in the X-ray powder diffraction pattern ±0.2:
9.7; 12.0; 18.0; 24.1; 25.9, with $I/I_0$ ratios as characterized in the following

| Peak | 2-theta | Intensity (cps) | $I/I_0$ |
|---|---|---|---|
| 1 | 6.0 | 4082 | 40 |
| 2 | 9.7 | 797 | 8 |
| 3 | 11.0 | 640 | 7 |
| 4 | 12.0 | 8297 | 80 |
| 5 | 17.6 | 2032 | 20 |
| 6 | 18.0 | 2173 | 21 |
| 7 | 18.7 | 2658 | 26 |
| 8 | 18.9 | 3293 | 32 |
| 9 | 19.6 | 919 | 9 |
| 10 | 20.7 | 7158 | 69 |
| 11 | 21.6 | 2730 | 27 |
| 12 | 22.2 | 2601 | 26 |
| 13 | 23.4 | 3261 | 32 |
| 14 | 24.1 | 10380 | 100 |
| 15 | 24.7 | 1663 | 17 |
| 16 | 25.9 | 5534 | 54 |
| 17 | 26.2 | 1771 | 18 |
| 18 | 28.2 | 1889 | 19. |

2. Polymorphic Form A according to claim 1 having the following peaks at the at the diffraction degrees in the X-ray powder diffraction pattern ±0.2:

| Peak | 2-theta | $I/I_0$ |
|---|---|---|
| 1 | 6.0 | 40 |
| 2 | 9.7 | 8 |
| 3 | 11.0 | 7 |
| 4 | 12.0 | 80 |
| 5 | 17.6 | 20 |
| 6 | 18.0 | 21 |
| 7 | 18.7 | 26 |
| 8 | 18.9 | 32 |
| 9 | 19.6 | 9 |
| 10 | 20.7 | 69 |
| 11 | 21.6 | 27 |
| 12 | 22.2 | 26 |
| 13 | 23.4 | 32 |
| 14 | 24.1 | 100 |
| 15 | 24.7 | 17 |
| 16 | 25.9 | 54 |
| 17 | 26.2 | 18 |
| 18 | 28.2 | 19. |

3. Polymorphic Form A according to claim 1 having the X-ray powder diffraction pattern depicted in FIG. 1.

4. A process for preparing the polymorphic Form A of N-[4-(trifluoromethyl)benzyl]-4-methoxybutyramide of claims 1 comprising the following steps:
   i) reacting 4-trifluoromethylbenzylamine with methyl 4-methoxybutyrate in the presence of a catalyst thus obtaining crude N-[4-(trifluoromethyl)benzyl]-4-methoxybutyramide; and
   (ii) obtaining crystalline polymorphic Form A from a solution of crude N-[4-(trifluoromethyl)benzyl]-4-methoxybutyramide in a organic solvent, being said solution seeded with the polymorphic Form A of N-[4-(trifluoromethyl)benzyl]-4-methoxybutyramide.

5. The process according to claim 4 wherein 4-trifluoromethylbenzyl amine is prepared by reacting 4-trifluoromethylbenzaldehyde with hydroxylamine HCl according to the following steps:
   i) reacting 4-trifluoromethylbenzaldehyde with hydroxylamine HCl to obtain 4-trifluoromethylbenzaldoxime; and
   (ii) obtaining 4-trifluoromethylbenzylamine by reduction of 4-trifluoromethylbenzaldoxime

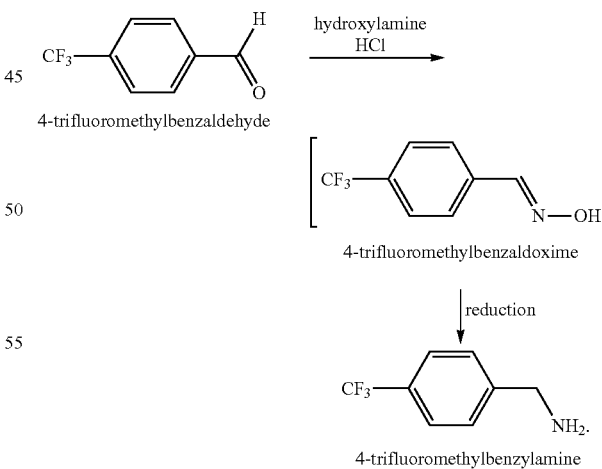

6. The process according to any one of claims 4, wherein, in the step (i), the catalyst is a 30% sodium methylate solution in methanol.

7. The process according to claim 4, wherein the organic solvent is selected from toluene and a mixture of ethylacetate/n-hexane.

8. The process according to claim 7, wherein the organic solvent is a mixture of ethylacetate/n-hexane.

9. The process according to claim 8, wherein the mixture of ethylacetate:n-hexane is in a ratio from 1:4 to 1:2.

10. A pharmaceutical composition comprising as active agent an effective amount of the polymorphic Form A of N[4-(trifluoromethyl)benzyl]-4-methoxybutyramide according to claim 1 and a pharmaceutically acceptable carrier.

11. The pharmaceutical composition according to claim 10, wherein the compound in polymorphic Form A, is in amount from 12.5 to 50% by weight.

12. Method for the treatment of drug addiction and alcoholism comprising administering to a subject in need thereof the polymorphic Form A of N-[4-(trifluoromethyl)benzyl]-4-methoxybutyramide according to claim 1.

13. The method according to claim 12 in reducing the voluntary consumption of ethyl alcohol and/or in the treatment of the abstinences syndrome.

14. The method according to claim 12, wherein the polymorphic Form A of N-[4-(trifluoromethyl)benzyl]-4-methoxybutyramide is in a dose from 5 to 50 mg/kg.

15. The method according to claim 14 wherein the polymorphic Form A of N-[4-(trifluoromethyl)benzyl]-4-methoxybutyramide is in a dose from 5 to 10 mg/kg.

16. The process according to claim 9, wherein the mixture of ethylacetate : n-hexane is in a ratio of about 1:3.

* * * * *